US010052207B2

(12) United States Patent
Chernosky et al.

(10) Patent No.: US 10,052,207 B2
(45) Date of Patent: Aug. 21, 2018

(54) FASTENER SYSTEM

(71) Applicant: Zimmer, Inc., Warsaw, IN (US)

(72) Inventors: John Chernosky, Brick, NJ (US); Keith A. Roby, Jersey City, NJ (US); Ray Zubok, North Haledon, NJ (US)

(73) Assignee: Zimmer, Inc., Warsaw, IN (US)

( * ) Notice: Subject to any disclaimer, the term of this patent is extended or adjusted under 35 U.S.C. 154(b) by 12 days.

(21) Appl. No.: 15/035,405

(22) PCT Filed: Nov. 13, 2014

(86) PCT No.: PCT/US2014/065362
§ 371 (c)(1),
(2) Date: May 9, 2016

(87) PCT Pub. No.: WO2015/073617
PCT Pub. Date: May 21, 2015

(65) Prior Publication Data
US 2016/0324644 A1 Nov. 10, 2016

Related U.S. Application Data

(60) Provisional application No. 61/903,731, filed on Nov. 13, 2013, provisional application No. 61/903,748, filed on Nov. 13, 2013.

(51) Int. Cl.
*A61F 2/38* (2006.01)
*A61F 2/30* (2006.01)

(52) U.S. Cl.
CPC .......... *A61F 2/389* (2013.01); *A61F 2/30734* (2013.01); *A61F 2002/30433* (2013.01);
(Continued)

(58) Field of Classification Search
CPC ................ A61F 2/36; A61F 2220/0041; A61F 2220/00; A61F 2/30734; A61F 2/389;
(Continued)

(56) References Cited

U.S. PATENT DOCUMENTS 4,878,791 A * 11/1989 Kurihara ................. F16B 29/00
411/41
4,944,757 A 7/1990 Martinez et al.
(Continued)

FOREIGN PATENT DOCUMENTS

DE 19741087 A1 4/1999
DE 10253888 A1 7/2005
(Continued)

OTHER PUBLICATIONS

"International Application Serial No. PCT/US2014/065362, International Search Report dated Feb 12, 2015", 5 pgs.
(Continued)

*Primary Examiner* — Alvin Stewart
(74) *Attorney, Agent, or Firm* — Schwegman Lundberg & Woessner, P.A.

(57) ABSTRACT

Fastener systems and methods for attaching two or more parts are disclosed. A fastener can include a nut component configured to extend into at least a portion of an aperture in a first part and at least a portion of an aperture in a second part. The fastener can further include a compression body configured to fit into an enlarged portion of the aperture in the second part, and a screw component having a head portion configured to engage with a top notch formed in the compression body and an elongated portion configured to engage with the nut component. A diameter of the head portion of the screw component can be less than a diameter of the top notch in the compression body such that the screw component can move in a radial direction relative to the compression body during placement of the fastener to attach two or more parts.

18 Claims, 5 Drawing Sheets

(52) U.S. Cl.
CPC .............. *A61F 2002/30434* (2013.01); *A61F 2002/30436* (2013.01); *A61F 2002/30438* (2013.01); *A61F 2002/30443* (2013.01); *A61F 2220/0041* (2013.01)

(58) Field of Classification Search
CPC .. A61F 2002/30433; A61F 2002/30434; A61F 2002/30436; A61F 2002/30438
See application file for complete search history.

(56) References Cited

U.S. PATENT DOCUMENTS

| | | | |
|---|---|---|---|
| 4,952,106 A * | 8/1990 | Kubogochi | F16B 19/1081 411/48 |
| 5,019,103 A * | 5/1991 | Van Zile | A61F 2/30734 623/20.34 |
| 5,152,797 A | 10/1992 | Luckman et al. | |
| 5,226,917 A * | 7/1993 | Schryver | A61B 17/68 623/22.18 |
| 5,275,603 A | 1/1994 | Ferrante et al. | |
| 5,370,693 A | 6/1994 | Kelman et al. | |
| 5,387,241 A | 2/1995 | Hayes | |
| 5,458,637 A | 10/1995 | Hayes | |
| 5,549,689 A | 8/1996 | Epstein et al. | |
| 5,702,464 A | 12/1997 | Lackey et al. | |
| 5,984,969 A * | 11/1999 | Matthews | A61F 2/30734 623/20.11 |
| 6,005,018 A * | 12/1999 | Cicierega | A61F 2/30734 623/20.16 |
| 6,074,424 A | 6/2000 | Perrone, Jr. et al. | |
| 6,139,581 A | 10/2000 | Engh et al. | |
| 6,214,052 B1 | 4/2001 | Burkinshaw | |
| 6,896,702 B2 | 5/2005 | Collazo | |
| 7,175,665 B2 | 2/2007 | German et al. | |
| 7,329,260 B2 | 2/2008 | Auger et al. | |
| 7,442,196 B2 | 10/2008 | Fisher et al. | |
| 7,578,821 B2 | 8/2009 | Fisher et al. | |
| 7,740,662 B2 | 6/2010 | Barnett et al. | |
| 7,842,093 B2 | 11/2010 | Peters et al. | |
| 7,842,094 B2 * | 11/2010 | Le Bon | A61F 2/30724 623/22.21 |
| 8,016,891 B2 | 9/2011 | Ensign | |
| 8,083,746 B2 | 12/2011 | Novak | |
| 8,128,627 B2 | 3/2012 | Justin et al. | |
| 8,262,329 B2 | 9/2012 | Wille | |
| 8,443,493 B2 * | 5/2013 | Seidel | F16B 5/0628 24/290 |
| 8,572,818 B2 * | 11/2013 | Hofmann | B60R 13/0206 24/297 |
| 8,932,364 B2 | 1/2015 | Mooradian et al. | |
| 9,144,495 B2 | 9/2015 | Lin et al. | |
| 9,241,801 B1 | 1/2016 | Parry et al. | |
| 9,333,554 B2 * | 5/2016 | Kanie | F16B 19/1081 |
| 9,408,699 B2 | 8/2016 | Stalcup et al. | |
| 2003/0074078 A1 * | 4/2003 | Doubler | A61F 2/36 623/22.42 |
| 2004/0225368 A1 | 11/2004 | Plumet et al. | |
| 2005/0055097 A1 | 3/2005 | Grunberg et al. | |
| 2006/0010690 A1 * | 1/2006 | Bogue | A61F 2/5046 29/898.049 |
| 2006/0015184 A1 | 1/2006 | Winterbottom et al. | |
| 2007/0088443 A1 | 4/2007 | Hanssen et al. | |
| 2008/0051908 A1 | 2/2008 | Angibaud et al. | |
| 2009/0171396 A1 | 7/2009 | Baynham et al. | |
| 2011/0009974 A1 | 1/2011 | Blaylock et al. | |
| 2011/0112651 A1 | 5/2011 | Blaylock et al. | |
| 2011/0190888 A1 | 8/2011 | Bertele et al. | |
| 2011/0190899 A1 | 8/2011 | Pierce et al. | |
| 2012/0185053 A1 | 7/2012 | Berger | |
| 2012/0209391 A1 | 8/2012 | Cipolletti et al. | |
| 2012/0310361 A1 * | 12/2012 | Zubok | A61F 2/30734 623/20.32 |
| 2013/0006370 A1 | 1/2013 | Wogoman et al. | |
| 2013/0013076 A1 | 1/2013 | Fisher et al. | |
| 2013/0261505 A1 | 10/2013 | Sherman | |
| 2013/0261759 A1 | 10/2013 | Claypool et al. | |
| 2014/0081408 A1 | 3/2014 | Lieberman et al. | |
| 2014/0172112 A1 | 6/2014 | Marter | |
| 2014/0222155 A1 | 8/2014 | Metzger et al. | |
| 2014/0222156 A1 | 8/2014 | Nevins et al. | |
| 2014/0277529 A1 | 9/2014 | Stalcup | |
| 2014/0277539 A1 | 9/2014 | Cook et al. | |
| 2014/0296859 A1 | 10/2014 | Claypool et al. | |
| 2014/0358242 A1 | 12/2014 | Mines | |
| 2015/0057758 A1 | 2/2015 | Axelson, Jr. | |
| 2015/0105782 A1 | 4/2015 | D'lima et al. | |
| 2016/0278925 A1 | 9/2016 | Roby et al. | |

FOREIGN PATENT DOCUMENTS

| | | |
|---|---|---|
| DE | 202008011163 U1 | 1/2009 |
| EP | 2319460 A1 | 5/2011 |
| WO | WO-2013134333 A1 | 9/2013 |
| WO | WO-2015073617 A1 | 5/2015 |
| WO | WO-2015073618 A1 | 5/2015 |

OTHER PUBLICATIONS

"International Application Serial No. PCT/US2014/065362, Written Opinion dated Feb. 12, 2015", 5 pgs.
"International Application Serial No. PCT/US2014/065363, International Search Report dated Jan. 28, 2015", 6 pgs.
"International Application Serial No. PCT/US2014/065363, Written Opinion dated Jan. 28, 2015", 7 pgs.
"U.S. Appl. No. 15/035,402, Non Final Office Action dated May 25, 2017", 10 pgs.
"U.S. Appl. No. 15/035,402, Preliminary Amendment filed May 9, 2016", 7 pgs.
"U.S. Appl. No. 15/035,402, Response filed Aug. 25, 2017 to Non Final Office Action dated May 25, 2017", 17 pgs.
"European Application Serial No. 14812329.2, Response filed Feb. 20, 2017 to Communication pursuant to Rules 161(1) and 162 EPC mailed Aug. 9, 2016", 17 pgs.
"European Application Serial No. 14816467.6, Response filed Feb. 20, 2017 to Communication pursuant to Rules 161(1) and 162 EPC mailed Aug. 9, 2016", 16 pgs.
"International Application Serial No. PCT/US2014/065362, International Preliminary Report on Patentability dated May 26, 2016", 7 pgs.
"International Application Serial No. PCT/US2014/065363, International Preliminary Report on Patentability dated May 26, 2016", 9 pgs.
"European Application Serial No. 14812329.2, Communication Pursuant to Article 94(3) EPC mailed Oct. 16, 2017", 5 pgs.

* cited by examiner

FASTENER SYSTEM

CLAIM OF PRIORITY

This application is a U.S. National Stage Application under 35 U.S.C. 371 from International Application No. PCT/US2014/065362, filed Nov. 13, 2014, and published as WO 2015/073617 A1 on May 21, 2015, which claims the benefit of U.S. Provisional Patent Application Ser. No. 61/903,731, filed on Nov. 13, 2013 and also claims the benefit of U.S. Provisional Patent Application Ser. No. 61/903,748, filed on Nov. 13, 2013, the benefit of priority of each of which is claimed hereby, and each of which are incorporated by reference herein in its entirety.

TECHNICAL FIELD

The present patent application relates to a fastener system, and, more particularly, to a fastener system usable for attaching two or more parts having one or more attachments points.

BACKGROUND

Fasteners are known and common for attaching two or more parts together. For example, fasteners can be used to attach two components of an orthopedic implant. Apertures on each of the parts are aligned with one another and the fastener is inserted through the apertures.

Variability in a size or location of the apertures on each of the parts can cause problems with alignment of the apertures, and thus problems in inserting and securing the fastener within the apertures. Any such variances can be more problematic or compounded if multiple fasteners are used for multiple attachment points on each of the parts.

OVERVIEW

The present inventors recognize, among other things, an opportunity for a fastener system for attaching two or more parts together that can provide some flexibility and can allow for greater tolerances in aligning the apertures, while still achieving sufficient attachment of the two or more parts.

To better illustrate the fastener system and methods disclosed herein, the following non-limiting examples are provided:

In Example 1, a fastener configured for attaching two or more parts to each other can comprise a first component, a second component and a third component. The first component can have a bottom portion configured to extend into at least a portion of an aperture in a first part, a top portion configured to extend into at least a portion of an aperture in a second part, and an opening formed through the top portion and at least a portion of the bottom portion. The second component can be configured to extend into an enlarged portion of the aperture in the second part and can comprise an opening formed from a top end to a bottom end of the second component, and a top notch formed in the top end and defining a top diameter. The third component can comprise a head portion having a head diameter and configured to engage with the top notch of the second component, and an elongated portion configured to extend through the opening of the second component and into the opening of the first component. The head diameter can be less than the top diameter of the second component such that the third component can move in a radial direction relative to the second component during placement of the fastener in the first and second parts.

In Example 2, the fastener of Example 1 can optionally be configured such that the bottom portion of the first component includes a feature formed on an exterior surface of the bottom portion and configured to engage with a feature formed in the aperture of the first part to secure the first component within at least a portion of the aperture of the first part and at least a portion of the aperture in the second part.

In Example 3, the fastener of Example 2 can optionally be configured such that the feature on the first component includes two or more notches formed on the exterior surface.

In Example 4, the fastener of any one or any combination of Examples 2 or 3 can optionally be configured such that the feature in the aperture of the first part includes a locking shoulder such that the first component initially compresses upon insertion into the aperture of the first part and then the first component releases from a compressed position such the first component is held in place against the locking shoulder.

In Example 5, the fastener of any one or any combination of Examples 1-4 can optionally be configured such that at least a part of the elongated portion of the third component includes threads on an exterior surface of the third component that engage with threads on an interior surface of the first component.

In Example 6, the fastener of any one or any combination of Examples 1-5 can optionally be configured such that the second component further comprises a bottom notch formed in the bottom end and defining a bottom diameter.

In Example 7, the fastener of Example 6 can optionally be configured such that an exterior diameter of the top portion of the first component is less than the bottom diameter of the second component such that the first component can move in a radial direction relative to the second component during placement of the fastener in the first and second parts.

In Example 8, the fastener of any one or any combination of Examples 1-7 can optionally be configured such that a third part having an aperture extending from a top end to a bottom end is sandwiched between the first part and the second part, and the first component includes a middle portion, located between the bottom portion and the top portion, extending through the aperture in the third part.

In Example 9, the fastener of Example 8 can optionally be configured such that the opening in the first component is formed through the middle portion of the first component, and the elongated portion of the third component extends through the opening in the middle portion of the first component.

In Example 10, the fastener of any one or any combination of Examples 1-9 can optionally be configured such that the first, second and third components are pre-assembled prior to inserting the fastener into the apertures of the first and second parts.

In Example 11, the fastener or Example 10 can optionally be configured such that the first and third components are movable in a radial direction within the apertures in the first and second parts, after the pre-assembled fastener is inserted into the apertures and prior to tightening the third component relative to the first component.

In Example 12, the fastener of any one or any combination of Examples 1-11 can optionally be configured such that wherein the first and second parts are components of an orthopedic implant.

In Example 13, a fastener system for attaching two or more parts to each other can comprise one or more nut components of varying lengths, a compression component, and one or more screw components of varying lengths. Each nut component can have an opening formed through a top portion of the nut component and extending into a bottom portion of the nut component, and each nut component can be configured to be inserted into at least a portion of an aperture in a first part and at least a portion of an aperture in a second part. Each screw component can include a head portion having a head diameter and configured to engage with the top notch formed in the compression component, and an elongated portion configured to extend through the opening of the compression component and into the opening of the nut component selected from the one or more nut components. The head diameter of the head portion of the one or more screw components can be less than the top diameter of the compression component such that each screw component can move in a radial direction relative to the compression component during insertion of the fastener system in the first and second parts, and a selection of the nut component and the screw component can be based on a total thickness of the two or more parts.

In Example 14, the fastener system of Example 13 can optionally be configured such that each nut component includes a bottom portion that includes a feature formed on an exterior surface of the nut component and configured to engage with a feature formed in the aperture of the first part to secure the nut component within at least a portion of the aperture of the first part and at least a portion of the aperture in the second part.

In Example 15, the fastener system of Example 14 can optionally be configured such that the feature on the nut component includes two or more notches formed on the exterior surface, and the feature in the aperture of the first part includes a locking shoulder such that the nut component initially compresses upon insertion into the aperture of the first part and then the nut component releases from a compressed position such the nut component is held in place against the locking shoulder.

In Example 16, the fastener system of any one or any combination of Examples 13-15 can optionally be configured such that the compression component includes a bottom notch formed in the bottom end and defining a bottom diameter.

In Example 17, the fastener system of Example 16 can optionally be configured such that each nut component includes a bottom portion configured to be inserted into at least a portion of the aperture in the first part and a top portion configured to be inserted into at least a portion of the aperture in the second part, and an exterior diameter of the top portion of the nut component is less than the bottom diameter of the compression component such that the nut component can move in a radial direction relative to the compression component during insertion of the fastener system in the first and second parts.

In Example 18, the fastener system of any one or any combination of Examples 13-17 can optionally be configured such that a third part having an aperture extending from a top end to a bottom end is sandwiched between the first part and the second part, and the nut component includes a middle portion, located between the bottom portion and the top portion, extending through the aperture in the third part.

In Example 19, the fastener system of any one or any combination of Examples 13-18 can optionally be configured such that the first and second parts are components of an orthopedic implant.

In Example 20, the fastener system of Example 19 can optionally be configured such that the first part is a tibial baseplate and the second part is an augment attachable to an underside of the tibial baseplate.

In Example 21, the fastener system of any one or any combination of Examples 13-20 can optionally be configured such that each of the first and second parts include multiple apertures extending through the first and second parts, and the first and second parts are configured to receive multiple fasteners for attaching the first and second parts to each other.

In Example 22, the fastener or systems of any one or any combination of Examples 1-21 can optionally be configured such that all elements or options recited are available to use or select from.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present application relates to fastener systems and methods for attaching two or more parts together. As described herein, a fastener system can include a nut, a compression body and a screw, and the fastener system can be inserted into corresponding holes or apertures formed in the two or more parts. In an example, the two or more parts can each include multiple sets of corresponding holes for receiving multiple fasteners. The components of the fastener system can be configured such that when the fastener system is initially inserted into the two or more parts, some of the components can have some movement prior to a final placement. This can be advantageous, for example, to compensate for potential misalignment of the corresponding holes of the two or more parts.

Figure 1A:
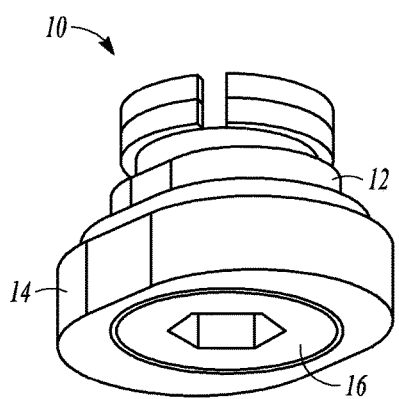
FIG. 1A is a perspective bottom view of an example of a fastener system in accordance with the present application.
Figure 1B:
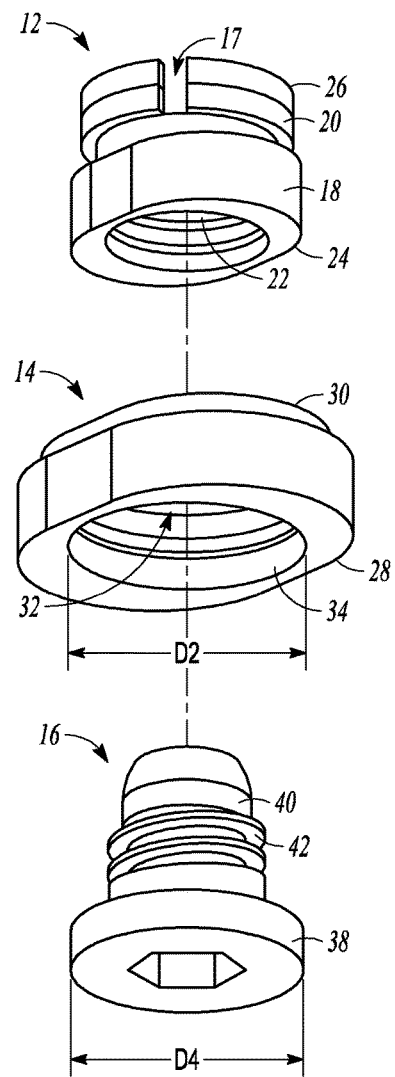
FIG. 1B is an exploded perspective view of the fastener system of FIG. 1A.
Figures 2A, 2B:
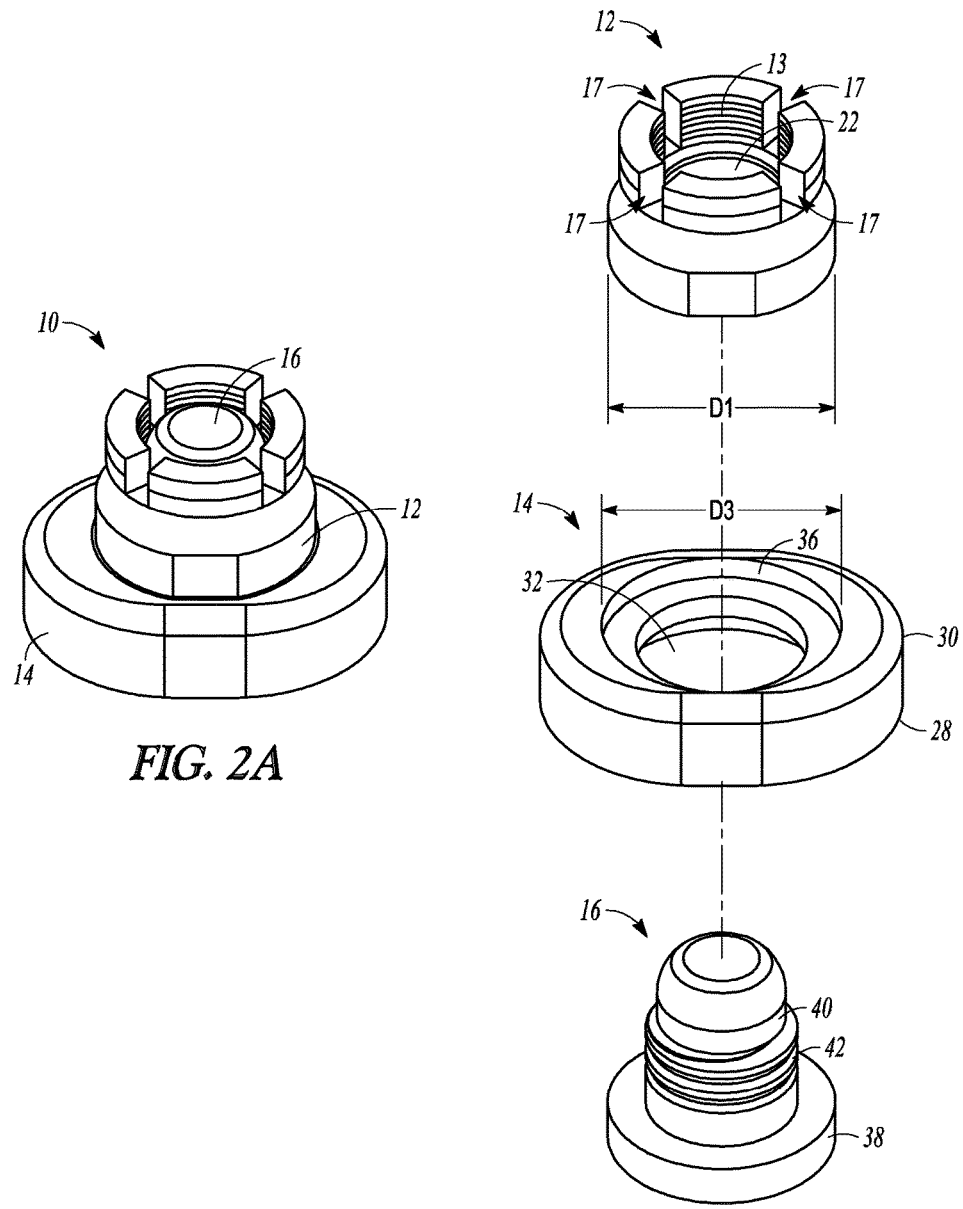
FIG. 2A is a perspective side view of the fastener system of FIGS. 1A-1B.
FIG. 2B is an exploded perspective view of the fastener system of FIG. 2A.

FIG. 1A shows an example of a fastener system 10, which can include a nut 12, a compression body 14, and a screw 16. FIG. 1B is an exploded perspective view of the fastener system 10. Similarly, FIGS. 2A and 2B are additional views of the fastener system 10 to show various features of the nut 12, the compression body 14, and the screw 16, which are described further below. The fastener system 10 can be configured such that during placement of the fastener system 10 for attaching two or more parts, the screw 16, and, in some cases, the nut 12, can 'float' or move relative to the compression body 14.

The nut 12 can include a top portion 18, a bottom portion 20, and an opening 22 formed through the top portion 18. In an example, as shown in FIGS. 1A-2B, the opening 22 can extend from a top end 24 to a bottom end 26 of the nut 12. In other examples, the opening 22 can extend from the top end 24 and into at least a part of the bottom portion 20 of the nut 12. The top portion 18 of the nut 12 can have an exterior diameter D1. An interior surface 13 of the nut 12 can include threads formed in at least a portion of the interior surface 13.

The bottom portion 20 of the nut 12 can include one or more notches or cut-outs 17 that can be configured to engage with a feature formed on an interior of one of the parts that the fastener system 10 is intended to hold together, as discussed further below. In an example, the nut 12 can include four notches 17 that can be spaced generally equidistant apart. In other examples, the nut 12 can include more or less notches 17, or the notches 17 can be larger or smaller than shown, relative to an overall size of the nut 12. Other features can be used in addition to or as an alternative to the notches 17 to engage with the interior of the part.

The compression body 14 can include a top end 28, a bottom end 30, and an opening 32 formed from the top end 28 to the bottom end 30. The compression body 14 can have a top notch 34 formed in the opening 32 at the top end 28, which is discussed further below. The top notch 34 can define an interior top diameter D2. In an example, the compression body 14 can have a bottom notch 36 formed in the opening 32 at the bottom end 30, which can define an interior bottom diameter D3. The top portion 18 of the nut 12 can extend into the bottom notch 36 when the fastener system 10 is assembled. The exterior diameter D1 of the top portion 18 of the nut 12 can be less than the bottom diameter D3 of the compression body 14. In other examples, the compression body 14 can exclude the bottom notch 36, in which case the nut 12 does not extend into the body 14, and the top portion 18 of the nut 12 can contact, or be near, the compression body 14 at the bottom end 30 of the compression body 14 when the fastener system 10 is assembled.

The screw 16 can include a head portion 38 and an elongated portion 40. The head portion 38 can have an exterior head diameter D4 and can be configured to engage with the top notch 34 in the compression body 14. The head diameter D4 can be less than the top diameter D2 of the compression body, as discussed further below. At least a portion of the elongated portion 40 of the screw 16 can include threads 42 that can engage with the threads on the interior surface 13 of the nut 12. The threads 42 on the screw 16 and the threads on the interior surface 13 of the nut 12 are examples of locking or securement features for the nut 12 and screw 16. It is recognized that other types of features can be used in addition to or as an alternative to the threading on the nut 12 and the screw 16, such as, for example, a key and groove combination, or other types of features that generally create a lock once the two components are fully engaged.

The nut 12, compression body 14, or screw 16 can be formed from any material or combination of materials suitable for implantation in a human or animal body. These materials can include plastic, stainless steel, aluminum, titanium, cobalt or one or more alloys thereof.

As described above, the head diameter D4 of the screw 16 can be less than the top diameter D2 of the compression body 14. As such, the screw 16 can move in a radial direction relative to the compression body 14 during placement of the fastener system 10 into one or more parts for attaching the one or more parts together. Similarly, in an example in which the compression body 14 includes the bottom notch 36, the diameter D1 of the nut 12 can be less than the bottom diameter D3 of the compression body 14 such that the nut 12 can move in a radial direction relative to the compression body 14 during placement of the fastener system 10. This design of the fastener system 10 can make the fastener system 10 well suited for attaching two or more parts together, including when the two or more parts have multiple apertures configured to receive multiple fasteners.

Figure 3:
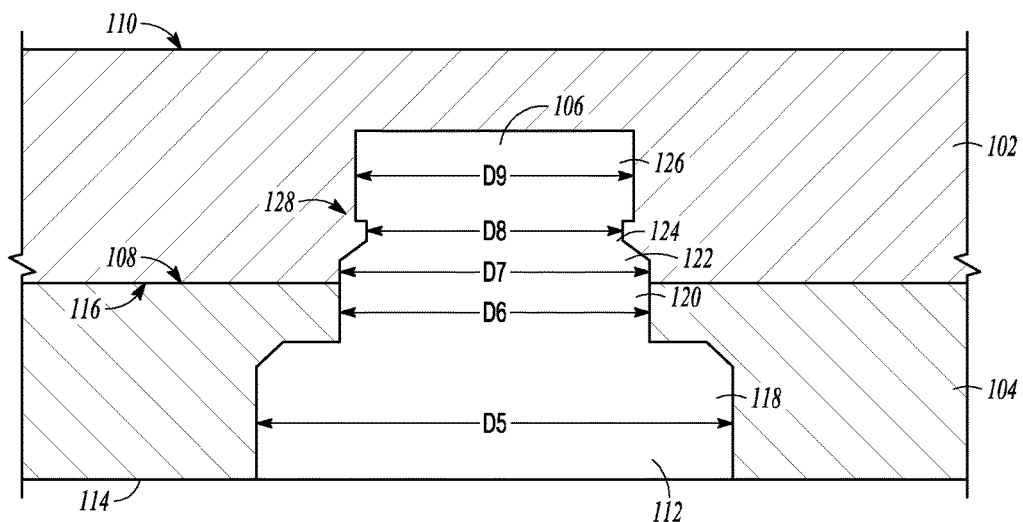
FIG. 3 is a cross-sectional view of a portion of two parts configured to be attached together and having aligned apertures.

FIG. 3 is a cross-sectional view of a portion of a first part 102 and a portion of a second part 104. The first part 102 can have an aperture 106, as shown in FIG. 3, extending from a first end 108 and towards a second end 110. In another example, the aperture 106 can extend through to the second end 110. The second part 104 can have an aperture 112 extending from a first end 114 through to a second end 116. The apertures 106 and 112 can have generally circular shapes and can include one or more features for receiving the fastener system 10.

In an example, as shown in FIG. 3, the apertures 106 and 112 can be generally the same size (have generally equal diameters) at the second end 116 of the second part 104 and the first end 108 of the first part 102. In other examples, the apertures 106 and 112 can be different sizes, relative to one another, at the second end 116 of the second part 104 and the first end 108 of the first part 102. FIG. 3 shows the first part 102 and the second part 104 assembled together such that the apertures 106 and 112 are aligned prior to attachment of the first 102 and second 104 parts together using the fastener system 10. Although not shown in FIG. 3, the parts 102 and 104 can include one or more additional apertures, similar to the apertures 106 and 112, respectively, configured to receive additional fasteners.

The aperture 112 of the second part 104 can have a first portion 118 and a second portion 120. The first portion 118 can be configured to receive the compression body 14 of the fastener system 10 and the second portion 120 can be configured to receive at least a portion of the nut 12. As such, a diameter D5 of the first portion 118 can be greater than a diameter D6 of the second portion 120.

The aperture 106 of the first part 102 can have at least two portions having different diameters. In an example, the aperture 106 can have three portions—a first portion 122, a second portion 124, and a third portion 126. In an example, at least some of the first portion 122 can have a diameter D7 that can be generally equal to the diameter D6 of the second portion 120 of the aperture 112 of the second part 104. In other examples, the diameter D7 can be larger or smaller than the diameter D6. The second portion 124 of the aperture 106 can have a diameter D8 and at least some of the third portion 126 can have a diameter D9 that can be greater than the diameter D8. A difference in diameter at a junction of the second 124 and third 126 portions can create a locking shoulder 128, which is discussed further below in reference to FIG. 4. The locking shoulder 128 is an example of a feature formed in the aperture 106 for engaging with the fastener system 10—it is recognized that other types of locking features can be formed in the aperture 106.

Figure 4:
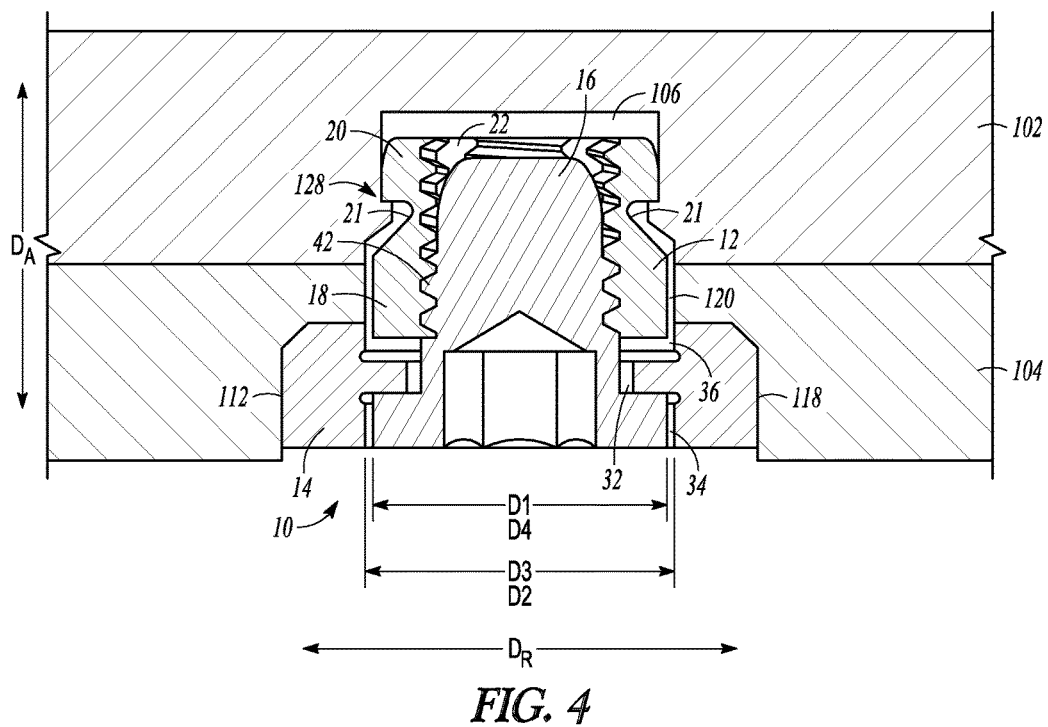
FIG. 4 is a cross-sectional view of the two parts of FIG. 3 and the fastener system of FIGS. 1A-2B inserted into the apertures of the two parts.

FIG. 4 shows the first 102 and second 104 parts of FIG. 3 with the fastener system 10 of FIGS. 1A-2B in an assembled position in which the first 102 and second 104 parts are attached to each other. As shown in FIG. 4, the compression body 14 can be sized and shaped to fit within the first portion 118 of the aperture 112 of the second part 104; the nut 12 can be sized and shaped to fit generally within the second portion 120 of the aperture 112 of the second part 104 and within the aperture 106 of the first part 102; and the screw 16 can be sized and shaped to be inserted into the compression body 14 and the nut 12. The compression body 14 can be sized and shaped such that the compression body 14 can have a 'tight fit' within the first portion 118 of the aperture 112. Once the compression body 14 is inserted into the aperture 112, the compression body 14 can have little to no movement within the aperture 112.

As described above, the nut 14 can include one or more features, like the notches 17. The notches 17 can engage with the locking shoulder 128 formed in the aperture 106 to secure the nut 12 within at least a portion of the aperture 106 of the first part 102 and at least a portion of the aperture 112 of the second part 104. Given a design of the nut 12 having the notches 17, the nut 12 can compress as it is inserted through the aperture 106 such that the bottom portion 20 of the nut 12 can pass through the second portion 124 of the aperture 106 having the reduced diameter D8, as compared to the adjacent portions 122 and 126 having the diameters D7 and D9 (see FIG. 3). At a later stage, the screw 16 can be tightened (in an example, the threads 42 on the screw 16 can engage with the threads on the interior surface 13 of the nut 12), which can spread apart the notches 17 and eliminate any compression of the notches 17. Once the screw 16 is tightened, the screw 16 can facilitate maintaining the nut 12 in its original uncompressed state, in which case the locking shoulder 128 can prevent the bottom portion 20 of the nut 12 from moving in an axial direction (labeled as $D_A$ in FIG. 4).

As described above, the diameter D1 of the top portion 18 of the nut 12 can be less than the diameter D3 of the bottom notch 36 of the compression body 14. As shown in FIG. 4, this can allow the top portion 18 of the nut 12 to move relative to the compression body 14 in a radial direction (labeled as $D_R$ in FIG. 4). In other examples, the bottom notch 36 can be excluded from a design of the compression body 14, in which case the top portion 18 of the nut 12 can generally contact, or be in close proximity to, the second end 30 of the compression body 14, rather than extend into a notch in the bottom of the compression body 14. The diameter D1 of the top portion 18 of the nut 12 can be less than the diameter D6 of the second portion 120 of the aperture 112; alternatively or in addition, the diameter D1 can be less than the diameter D7 of the first portion 122 of the aperture 106. As such, the nut 12 can move in the radial direction $D_R$ relative to the apertures 106 or 112.

As also described above, the diameter D4 of the screw 16 can be less than the diameter D2 of the top notch 34 of the compression body 14. As such, the screw 16 can move relative to the compression body 14 in the radial direction $D_R$. In an example, as shown in FIG. 4, the top diameter D1 of the nut 12 can be generally equal to the top diameter D4 of the screw. Similarly, in an example, as shown in FIG. 4, the diameter D2 of the top notch 34 can be generally equal to the diameter D3 of the bottom notch 36. In other examples, the diameter D1 can be less than or greater than the diameter D4, and the diameter D2 can be less than or greater than the diameter D3.

A method of using the fastener system 10 to attach two or more parts together can include pre-assembling the fastener system 10, or a portion thereof. In an example, the fastener system 10 can be pre-assembled prior to inserting the fastener system 10 into the apertures 106 and 112 of the first 102 and second 104 parts, respectively. In such an example, the nut 12 can be aligned with the compression body 14, and the screw 16 can be inserted into the nut 12 and the compression body 14 prior to inserting the fastener system 10 into the apertures 106 and 112. Upon insertion of the pre-assembled fastener system 10 into the apertures 106 and 112, the compression body 14 can have a tight fit within the aperture 112 and can be pressed into place. In contrast, given a diameter difference between the head diameter D4 of the screw 16 and the top diameter D2 of the compression body 14, the screw 16 can initially float after the pre-assembled fastener system 10 is inserted into the apertures 106 and 112. Similarly, given a diameter difference between the nut diameter D1 of the nut 12 and the bottom diameter D3 of the compression body 14, the nut 12 can initially float after the pre-assembled fastener system 10 is inserted into the apertures 106 and 112. The nut 12 and the screw 16 can each float, or move in a radial direction, within the apertures 106 and 112, until each is centered. The method can include tightening the screw 16, such that the threads 42 on the screw 16 can engage with the threads on the interior surface of the nut 12, thereby causing the screw 16 and the nut 12 to be locked into place, along with the compression body 14, within the apertures 106 and 112.

In another example, the components of the fastener system 10 are not pre-assembled and the method of using the fastener system 10 can include separately placing each of the components into the apertures 106 and 112, and then tightening the screw 16. The nut 12 can be first inserted into the first part 102 and then the compression body 14 can be inserted into the second part 104. The screw 16 can then be placed through the opening 32 of the compression body 14 and into the opening 22 of the nut 12. Next, the screw 16 can be tightened such that the fastener system 10 is locked in place. Similar to the description above in regard to the pre-assembled fastener system, if the components are individually placed into the apertures 106 and 112, the screw 16 and nut 12 can each be able to initially move in a radial direction such that the screw 16 and nut 12 can self-center.

By designing the fastener system 10 such that the screw 16, and in some examples the nut 12, can initially move relative to the compression body 14 and self-center, the fastener system 10 can be used even if the apertures 106 and 112 of the first 102 and second 104 parts, respectively, are not perfectly aligned with one another. This tolerance of the fastener system 10 can be beneficial when the parts 102 and 104 each have more than one aperture for attaching the two parts 102 and 104 together.

Figure 5:
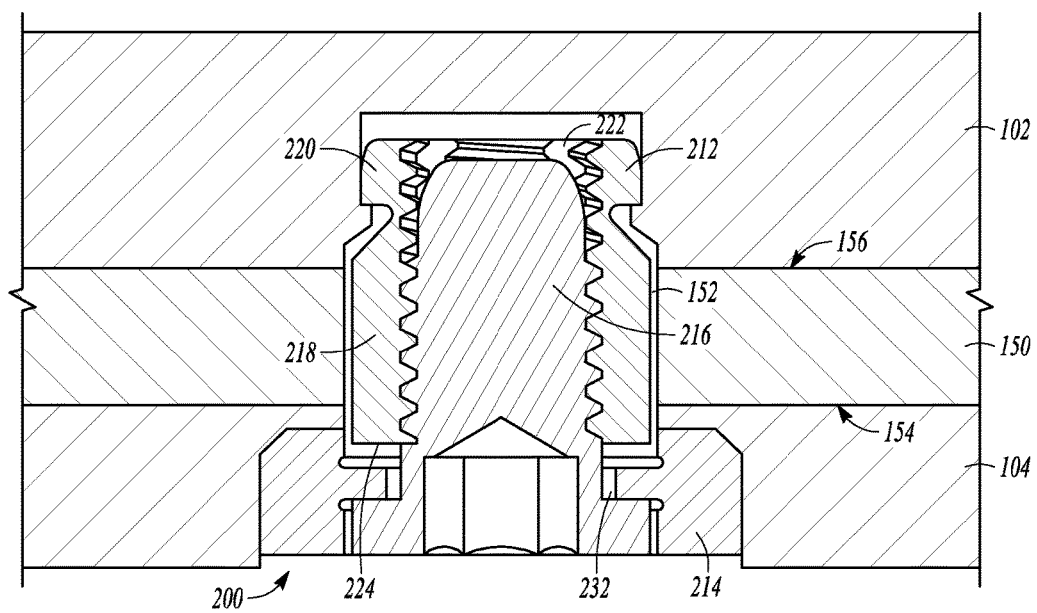
FIG. 5 is a cross-sectional view of a portion of three parts attached together using an example of a fastener system in accordance with the present application.

FIG. 5 shows an example of a fastener system 200 for attaching three parts to one another. The three parts can include the first 102 and second 104 parts of FIGS. 3 and 4, as well as a third part 150. The fastener system 200 can be similar to the fastener system 10 and can be configured for attaching two or more parts to each other. In an example, the fastener system 200 can be sized and shaped to attach three parts 102, 104 and 150 to one another. The fastener system 200 can include a nut 212, a compression body 214, and a screw 216.

In the example shown in FIG. 5, the third part 150 can be sandwiched between the first 102 and second 104 parts, and can have an aperture 152 extending from a top end 154 to a bottom end 156 of the third part 150. The aperture 152 can be configured to receive the nut 212. In an example, the aperture 152 can have a diameter at the ends 154 and 156 that can be generally similar in size to one or both of the diameters D6 and D7 at the ends 108 and 116 of the apertures 106 and 112, respectively.

The nut 212 can have a longer length as compared to the nut 12 of the fastener system 10, since the nut 212 can be configured to extend through the third part 150 and into the aperture 106 of the first part 102. In an example, as shown in FIG. 5, a top portion 218 of the nut 212 can be longer than the top portion 18 of the nut 12, to increase an overall length of the nut 212 relative to the nut 12. In an example, a bottom portion 220 of the nut 212 can be longer than the bottom portion 20 of the nut 12, to increase an overall length of the nut 212 relative to the nut 12. In other examples, a length of both the top portion 218 and the bottom portion 220 of the nut 212 can be increased, relative to a length of the top portion 18 and the bottom portion 20, respectively, of the nut 12, to increase an overall length of the nut 212.

Similar to the nut 12, the nut 212 can include an opening 222 that can extend from a top end 224 of the nut and into at least part of a bottom portion 220 of the nut 212. The screw 216 can be configured to extend through an opening 232 in the compression body 214 and into the opening 222 in the nut 212. The screw 216 can also have a longer length, as compared to the screw 16 of the fastener system 10, to correspond to the nut 212.

Features and diameters of the components of the fastener system 200 can be similar to those described above in reference to the components of the fastener system 10. The diameters of the components of the fastener system 200 can be sized and shaped to correspond with the apertures in the parts 102, 150, and 104.

Although two parts 102 and 104 are shown in FIGS. 3 and 4, and three parts 102, 104 and 150 are shown in FIG. 5, the fastener systems 10 and 200 described herein can be used for attaching any number of parts to each other. Moreover, the fastener systems 10 and 200 can be used for attaching any type of parts. As described above, the design of the fastener systems 10 and 200, including the radial movement of the screws relative to the compression body and the radial movement of the nuts relative to the compression body or at least one aperture of the parts, can make the fastener systems 10 and 200 well suited for attaching two or more parts together when there are multiple attachment points on each of the two or more parts. The tolerance created in the fastener systems 10 and 200 can be beneficial when the two or more parts have more than one set of apertures for attaching the parts together.

Figure 6:
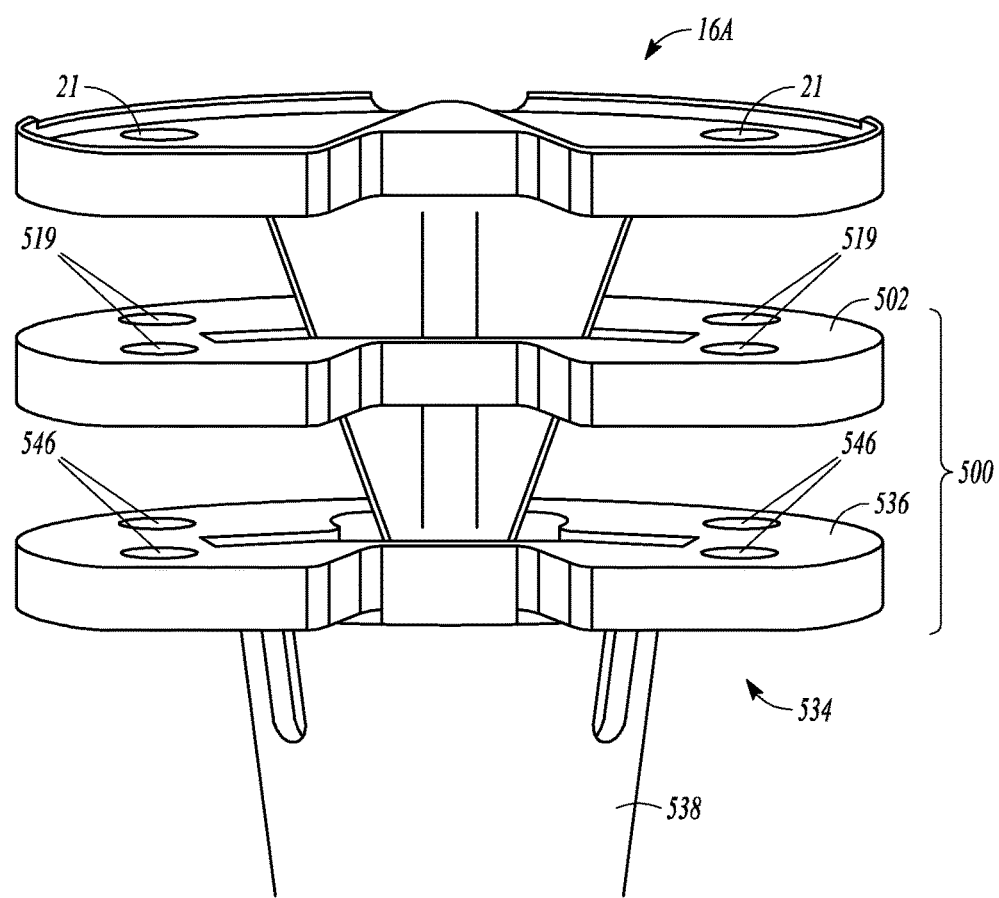
FIG. 6 is a an example of a tibial baseplate and an augment system that can be attached together using a fastener system in accordance with the present application.

In an example, the parts 102, 104 and 150 can be components of an orthopedic implant. FIG. 6 shows an example of a tibial baseplate 16A that can be used in a knee replacement surgical procedure in combination with other components, such as a bearing component and a femoral component. As shown in FIG. 6, an example of an augment system 500 can include a support structure 534, having a plate portion 536 and a medullary portion 538, and a plate 502 in stacked relation to the plate portion 536. The tibial baseplate 16A, the plate 502 and the support structure 534 can each include one or more holes 21, 519 and 546, respectively, for receiving a fastener to assemble the augment system 500 to the tibial baseplate 16A. In an example, each of the parts can include four apertures, which can correspond to four fasteners. It is recognized that more of less apertures can be included on each of the parts. The fastener system described herein can be used to attach the augment system 500 to the tibial baseplate 16A.

In an example, the parts 102, 150 and 104 of FIG. 5, can correspond to the tibial baseplate 16A, the first plate 502, and the plate portion 536, respectively, of FIG. 6. The fastener system 200 can be used to attach the tibial baseplate 16A, the first plate 502, and the plate portion 536 together. The fastener system 200 can be configured in a bottom to top orientation, as shown in FIG. 5. Alternatively, the fastener system 200 can be configured in a top to bottom orientation such that the compression body 214 can be inserted into the first part 102 and the screw 216 and nut 212 components can extend into the third 150 and second 104 parts. In another example, a fastener system, like the fastener system 10 of FIGS. 1-3, can be used to attach a single augment to a tibial baseplate. Reference is made to provisional application, U.S. Ser. No. 61/903,748, entitled "AUGMENT SYSTEM FOR AN IMPLANT", and directed to augment systems and methods for use with a tibial implant, which is incorporated by reference herein in its entirety.

In an example, a plurality of each of the components of the fastener system of the present application can be provided to a user as a system, which can be packaged together or separately. The components can be offered in a variety of sizes in order to be used with different types of parts intended to be attached together and with different sized or shaped apertures formed in the parts. A plurality of nuts can include nuts having different lengths to accommodate a number and thickness of the parts. The plurality of nuts can also include nuts having different diameters or shapes configured to be used in various size apertures formed in the parts. Similarly, a plurality of screws can include screws having different lengths and diameters to correspond with the plurality of nuts. A plurality of compression bodies can include compression bodies having different diameters or shapes to accommodate the nuts and screws, as well as different size apertures in the parts. Each of the nut, compression and screw components in the system can include the features described above and shown in the figures.

By having a plurality of fastener components available for use, the user can select a combination of components based on a particular situation. For example, if the fastener system is used in combination with an augment system for a tibial baseplate, the fastener components can change on demand as specific augment components are tested and selected for a particular patient. In an example, if all the augments and the corresponding tibial baseplate have generally the same size apertures for receiving the fastener system, various screws and nuts can be used as an overall thickness changes based on a thickness of the augment or augments selected. Thus the fastener system of the present application offers flexibility to the user. In addition, because the nut and screw are configured to float relative to the compression body, when the fastener system is initially inserted into the apertures of the parts, the nut and screw can compensate for potential misalignment of the apertures of each part relative to each other. This can be beneficial when, for example, each of the parts has multiple apertures, configured for multiple fasteners, as shown for the tibial baseplate and augment system of FIG. 6.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A fastener configured for attaching two or more parts to each other, the fastener comprising:
   a first component comprising a compressible bottom portion configured to extend into at least a portion of an aperture in a first part, a top portion configured to extend into at least a portion of an aperture in a second part, and an opening formed through the top portion and at least a portion of the bottom portion;
   a second component configured to extend into an enlarged portion of the aperture in the second part and comprising an opening formed from a top end to a bottom end of the second component, and a top notch formed in the top end and defining a top diameter; and
   a third component comprising a head portion having a head diameter and configured to engage with the top notch of the second component, and an elongated portion configured to extend through the opening of the second component and into the opening of the first component, wherein the head diameter is less than the top diameter of the second component such that the third component can move in a radial direction relative to the second component during placement of the fastener in the first and second parts,
   wherein the bottom portion of the first component includes a feature formed on an exterior surface of the bottom portion and configured to engage with a corresponding feature formed in the aperture of the first part to secure the first component within at least a portion of the aperture of the first part and at least a portion of the aperture in the second part, and the feature includes two or more notches formed on the exterior surface of the bottom portion.

2. The fastener of claim 1, wherein the corresponding feature in the aperture of the first part includes a locking shoulder such that the first component initially compresses upon insertion into the aperture of the first part and then the first component releases from a compressed position such the first component is held in place against the locking shoulder.

3. The fastener of claim 1, wherein at least a part of the elongated portion of the third component includes threads on an exterior surface of the third component that engage with threads on an interior surface of the first component.

4. The fastener of claim 1, wherein the second component further comprises a bottom notch formed in the bottom end and defining a bottom diameter.

5. The fastener of claim 4, wherein an exterior diameter of the top portion of the first component is less than the bottom diameter of the second component such that the first component can move in a radial direction relative to the second component during placement of the fastener in the first and second parts.

6. The fastener of claim 1, wherein a third part having an aperture extending from a top end to a bottom end is sandwiched between the first part and the second part, and the first component includes a middle portion, located between the bottom portion and the top portion, extending through the aperture in the third part.

7. The fastener of claim 6, wherein the opening in the first component is formed through the middle portion of the first component, and the elongated portion of the third component extends through the opening in the middle portion of the first component.

8. The fastener of claim 1, wherein the first, second and third components are pre-assembled prior to inserting the fastener into the apertures of the first and second parts.

9. The fastener of claim 8, wherein the first and third components are movable in a radial direction within the apertures in the first and second parts, after the pre-assembled fastener is inserted into the apertures and prior to tightening the third component relative to the first component.

10. The fastener of claim 1, wherein the first and second parts are components of an orthopedic implant.

11. A fastener system for attaching two or more parts to each other, the fastener system comprising:
   one or more nut components of varying lengths, each nut component having an opening formed through a top portion of the nut component and extending into a bottom portion of the nut component, and each nut component configured to be inserted into at least a portion of an aperture in a first part and at least a portion of an aperture in a second part;
   a compression component configured to be secured within the aperture in the second part and comprising an opening formed from a top end to a bottom end of the compression component, and a top notch formed in the top end and defining a top diameter; and
   one or more screw components of varying lengths, each screw component comprising a head portion having a head diameter and configured to engage with the top notch formed in the compression component, and an elongated portion configured to extend through the opening of the compression component and into the opening of the nut component selected from the one or more nut components,
   wherein the head diameter of the head portion of the one or more screw components is less than the top diameter of the compression component such that each screw component can move in a radial direction relative to the compression component during insertion of the fastener system in the first and second parts, and a selection of the nut component and the screw component is based on a total thickness of the two or more parts.

12. The fastener system of claim 11, wherein each nut component includes a bottom portion that includes a feature formed on an exterior surface of the nut component and configured to engage with a feature formed in the aperture of the first part to secure the nut component within at least a portion of the aperture of the first part and at least a portion of the aperture in the second part.

13. The fastener system of claim 12, wherein the feature on the nut component includes two or more notches formed on the exterior surface, and the feature in the aperture of the first part includes a locking shoulder such that the nut component initially compresses upon insertion into the aperture of the first part and then the nut component releases from a compressed position such the nut component is held in place against the locking shoulder.

14. The fastener system of claim 11, wherein the compression component includes a bottom notch formed in the bottom end and defining a bottom diameter.

15. The fastener system of claim 14, wherein each nut component includes a bottom portion configured to be inserted into at least a portion of the aperture in the first part and a top portion configured to be inserted into at least a portion of the aperture in the second part, and an exterior diameter of the top portion of the nut component is less than the bottom diameter of the compression component such that the nut component can move in a radial direction relative to the compression component during insertion of the fastener system in the first and second parts.

16. The fastener system of claim 11, wherein a third part having an aperture extending from a top end to a bottom end is sandwiched between the first part and the second part, and the nut component includes a middle portion, located between the bottom portion and the top portion, extending through the aperture in the third part.

17. The fastener system of claim 11, wherein the first and second parts are components of an orthopedic implant, the first part is a tibial baseplate and the second part is an augment attachable to an underside of the tibial baseplate.

18. The fastener system of claim 11, wherein each of the first and second parts include multiple apertures extending through the first and second parts, and the first and second parts are configured to receive multiple fasteners for attaching the first and second parts to each other.

* * * * *